(12) United States Patent
Bau-Madsen et al.

(10) Patent No.: US 11,193,949 B2
(45) Date of Patent: Dec. 7, 2021

(54) DIAGNOSTIC TEST READER SYSTEM

(71) Applicant: Zoetis Services LLC, Parsippany, NJ (US)

(72) Inventors: Niels Kristian Bau-Madsen, Hellerup (DK); Ole Kring, Birkerod (DK)

(73) Assignee: Zoetis Services LLC, Parsippany, NJ (US)

( * ) Notice: Subject to any disclaimer, the term of this patent is extended or adjusted under 35 U.S.C. 154(b) by 63 days.

(21) Appl. No.: 15/895,542

(22) Filed: Feb. 13, 2018

(65) Prior Publication Data

US 2018/0238918 A1    Aug. 23, 2018

Related U.S. Application Data

(60) Provisional application No. 62/461,316, filed on Feb. 21, 2017.

(51) Int. Cl.
*G01N 35/00* (2006.01)
*G01N 33/487* (2006.01)
*G05D 3/00* (2006.01)
*G06Q 10/08* (2012.01)
(Continued)

(52) U.S. Cl.
CPC . *G01N 35/00029* (2013.01); *G01N 33/48792* (2013.01); *G01N 35/00623* (2013.01); *G01N 35/00871* (2013.01); *G05D 3/00* (2013.01); *G01N 15/14* (2013.01); *G01N 2015/1006* (2013.01); *G01N 2035/009* (2013.01); *G01N 2035/00099* (2013.01); *G01N 2035/00306* (2013.01); *G01N 2035/00326* (2013.01);
(Continued)

(58) Field of Classification Search
None
See application file for complete search history.

(56) References Cited

U.S. PATENT DOCUMENTS

| 5,590,648 A | 1/1997 | Mitchell et al. |
| 2007/0268138 A1* | 11/2007 | Chung ............... G01S 5/0018 340/572.1 |
| 2011/0256638 A1 | 10/2011 | Chan et al. |

(Continued)

FOREIGN PATENT DOCUMENTS

| WO | WO 2015/099890 A2 | 7/2015 |
| WO | WO-2015099890 A2 * | 7/2015 |

(Continued)

OTHER PUBLICATIONS

Danish Patent and Trademark Office Search Report, Danish Patent Application No. PA 2017 70123, Date of completion of search report Aug. 25, 2017.

(Continued)

*Primary Examiner* — Matthew D Krcha
(74) *Attorney, Agent, or Firm* — Scott C. Mayhew

(57) ABSTRACT

A diagnostic test reader system including two or more reader modules and at least one mother module is provided. Each of the reader modules includes a unique code and is configured for reading a specific test cartridge type. Each of the reader modules is configured to be in data communication with the mother module for receiving instructions from the mother module and for transmitting read and/or derived data to the mother module. The mother module is configured for communicating individually with each of the reader modules.

19 Claims, 13 Drawing Sheets

(51) Int. Cl.
    *G01N 15/10* (2006.01)
    *G01N 15/14* (2006.01)
(52) U.S. Cl.
    CPC .............. *G01N 2035/00811* (2013.01); *G01N 2035/00891* (2013.01); *G06Q 10/08* (2013.01)

(56) References Cited

U.S. PATENT DOCUMENTS

| | | |
|---|---|---|
| 2012/0203465 A1 | 8/2012 | Callewaert et al. |
| 2013/0241737 A1 | 9/2013 | Davis et al. |
| 2015/0056719 A1 | 2/2015 | Karlovac et al. |

FOREIGN PATENT DOCUMENTS

| | | | | |
|---|---|---|---|---|
| WO | WO 2016/195896 A1 | 12/2016 | | |
| WO | WO 2016/203019 A1 | 12/2016 | | |
| WO | WO-2016195896 A1 * | 12/2016 | ....... | G01N 35/00693 |

OTHER PUBLICATIONS

International Search Report and Written Opinion, International Application No. PCT/US2018/018097, International Filing Date Feb. 14, 2018, dated May 24, 2018.

Oh, Y. K. et al., Mar. 7, 2013, "Vertical flow immunoassay (VFA) biosensor for a rapid one-step immunoassay," Lab on a Chip, vol. 13, pp. 768-772.

O'Connor, T. P., 2015, "SNAP Assay Technology," Topics in Compan An Med, vol. 30, pp. 132-138.

* cited by examiner

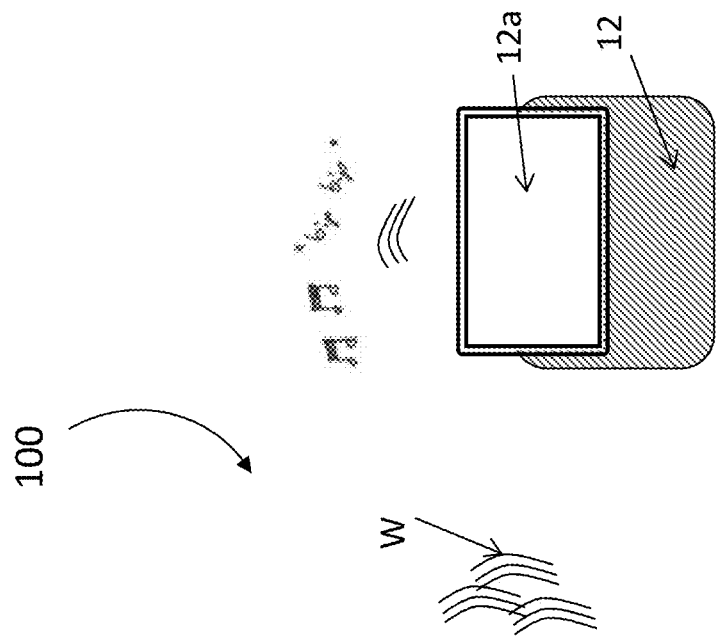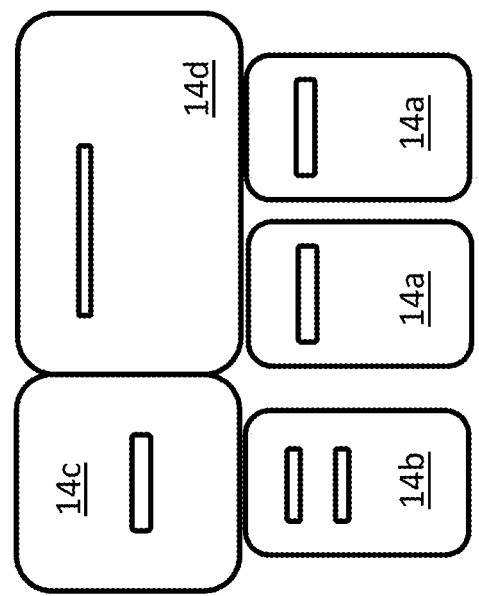
Fig. 4

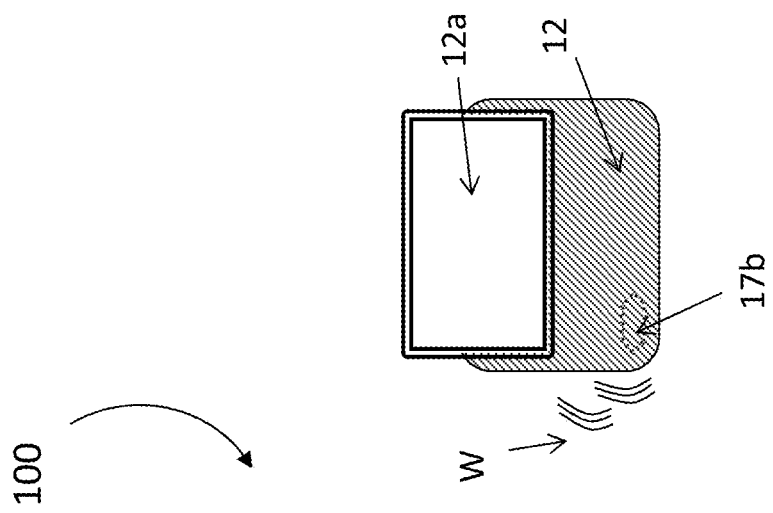
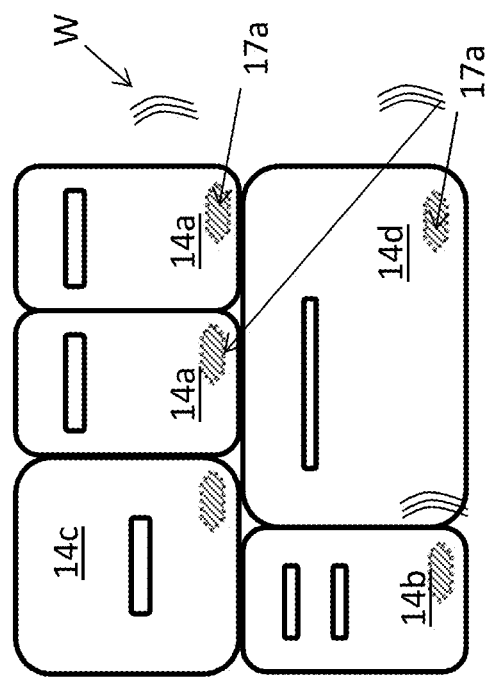
Fig. 7

Fig.10

Reader Module Database

| Unique code | Type of reader | Test to run | Time of test run | ..... |
|---|---|---|---|---|
| 1000100 | Lateral flow.... | Test A Test B ... | ... | |
| 101001 | Data... | Data... | ... | |
| 1001001 | Data... | Data... | ... | |
| ... | Data... | Data... | ... | |
| ... | ... | ... | ... | |

Fig.11

User Database

| User code | Name | Capacity | Employment data | Approved for |
|---|---|---|---|---|
| 101100 | John Doe | Assistant | .... | LF, VF I, VFII, ..... |
| 101011 | Data... | Veterinarian | ... | ..... |
| 1000011 | Data... | Veterinarian Trainee | ... | ..... |
| | Data... | Data... | ... | ..... |
| ... | ... | | ... | ..... |

Fig. 12

Diagnostic Cartridge Database

| Unique code | Cartridge type | Supplier | Batch no | Serial no. | Date of use | Operator used | Patient |
|---|---|---|---|---|---|---|---|
| 111001 | MF | xxxx | 122015 | 20001 | 20170112 | 101011 | 111011 |
| 111002 | MF | xxxx | 122015 | 20002 | | | |
| 110218 | VF | yyyy | 133416 | 218 | | | |
| 110219 | VF | yyyy | 133416 | 219 | | | |
| 101301 | LF | zzzz | 010101 | 301 | | | |
| ... | ... | ... | ... | ... | | | |

Fig.13

Patient Database

| User code | Animal | Owner | Species | Birthday | Treatments...Sympt oms..etc |
|---|---|---|---|---|---|
| 010101 | Dog | John Doe | Retriver | 20110305 | ... |
| 001000 | Dog | ... | Sheepdog | ... | ... |
| 110001 | Cat | ... | Persian | ... | ... |
| ... | Rabbit | ... | ... | ... | ... |
| ... | ... | ... | ... | ... | ... |

DIAGNOSTIC TEST READER SYSTEM

CROSS REFERENCE TO RELATED APPLICATION

This application claims the benefit of U.S. Provisional Patent Application No. 62/461,316, filed Feb. 21, 2017, which is expressly incorporated herein by reference in its entirety.

TECHNICAL FIELD

The present disclosure relates to a diagnostic test reader system suitable for reading different test cartridge types, such as a microfluidic test cartridge, a lateral flow test cartridge, a fluorescent test cartridge, a flow through test cartridge, and an electrical read our test cartridge.

BACKGROUND

In recent years, many different rapid diagnostic test methods and devices for performing biological assays on human and animal fluids have been developed. Examples of rapid diagnostic test types are lateral flow tests, microfluidic tests or flow through test types. The rapid diagnostic test types usually run for from a few seconds to one or more hours. For most of the rapid diagnostic test types it has been aimed to reduce the required running time. However, generally the rapid diagnostic test types are required to run for minutes. In laboratories and at veterinarian clinics, hospitals or doctor clinics many different rapid diagnostic test types are usually run several times each day or even more frequently. Many of the rapid diagnostic test types require a reader for ensuring a safe and accurate read out. For other rapid diagnostic test types the doctor or veterinarian prefers to have a reader to save time. Without a reader the doctor or veterinarian would need to observe the test run to ensure that the test is not corrupted, which could lead to false negative or false positive results.

The rapid diagnostic test types are usually performed using a cartridge comprising the assay elements required for performing the diagnostic assay, such as membrane test strip(s), flow channel(s), immobilized or non-immobilized binding partner(s), washing fluid(s) if required, markers, electrical wires, micro beads, magnetic beads and etc. For some test types the reader may comprise and be programmed to add fluids, e.g. washing fluid(s). Due to the many different types of rapid diagnostic test types, the clinics usually may be required to have several different types of readers of different size and with different functions. Often it is difficult for assistants to distinguish between the different types of readers and sometimes the readers are mixed up or misused due to mistakes. Also, it may be the case that a test for one patient is mixed up with a test from another patient.

The readers are often relatively small and may be moved around, for example during cleaning of the clinic. The moving around of the readers by a cleaner may result in further mistakes.

US2015056719 describes a universal rapid diagnostics test reader which can be used for different types of rapid diagnostic test types. The reader comprises control electronics, a digital camera component, an illumination component, a housing component, and a rapid diagnostics test tray, which tray can be modified or replaced in dependence on which test type is to be performed.

Thus, the reader comprises all electronics, reader functionalities and components for performing several types of tests. Generally such multifunctional reader types have the problem that they become rather complicated and bulky compared to normal diagnostic test readers. Further, in cases where the multifunctional reader is damaged or needs service, the clinic cannot perform any tests at all or may need to have several multifunctional readers. Further the constant change or modification of the tray for the reader and changes for performing different types of test is very complicated and may likely result in damage or misplacement of the tray(s) or tray element(s).

BRIEF SUMMARY

The above and other needs are met by aspects of the present disclosure which, according to one aspect, provides a diagnostic test reader system comprising a plurality of modules, including a plurality of reader modules and at least one mother module. Each of the reader modules has a unique code and is adapted for reading a specific test cartridge type. Each of the reader modules is adapted to be in data communication with the mother module for receiving instructions from said mother module and for transmitting read and/or derived data to said mother module. The mother module is configured for communicating individually with each of said reader modules.

Thus, various aspects of the present disclosure provide advantages, as otherwise detailed herein.

BRIEF DESCRIPTION OF THE DRAWINGS

Figure 1:
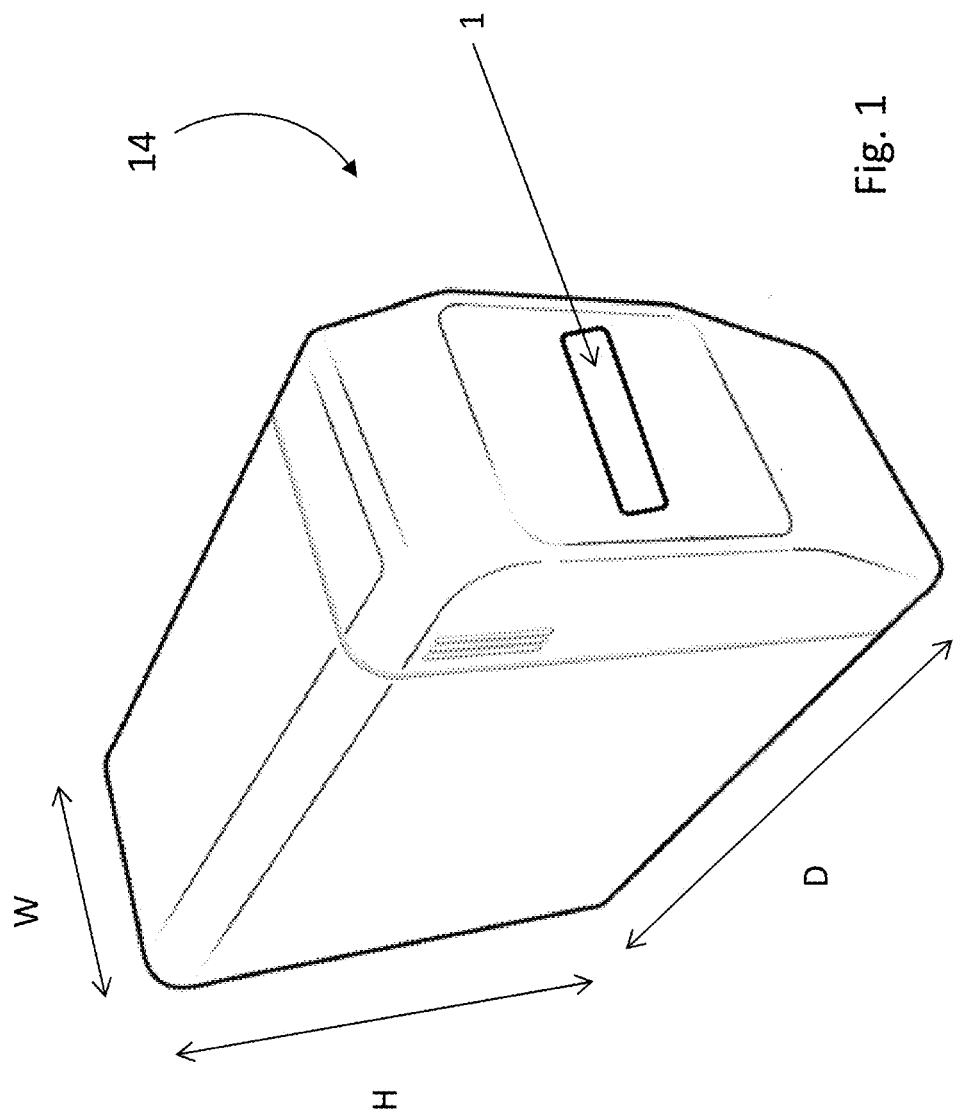
Figure 2:
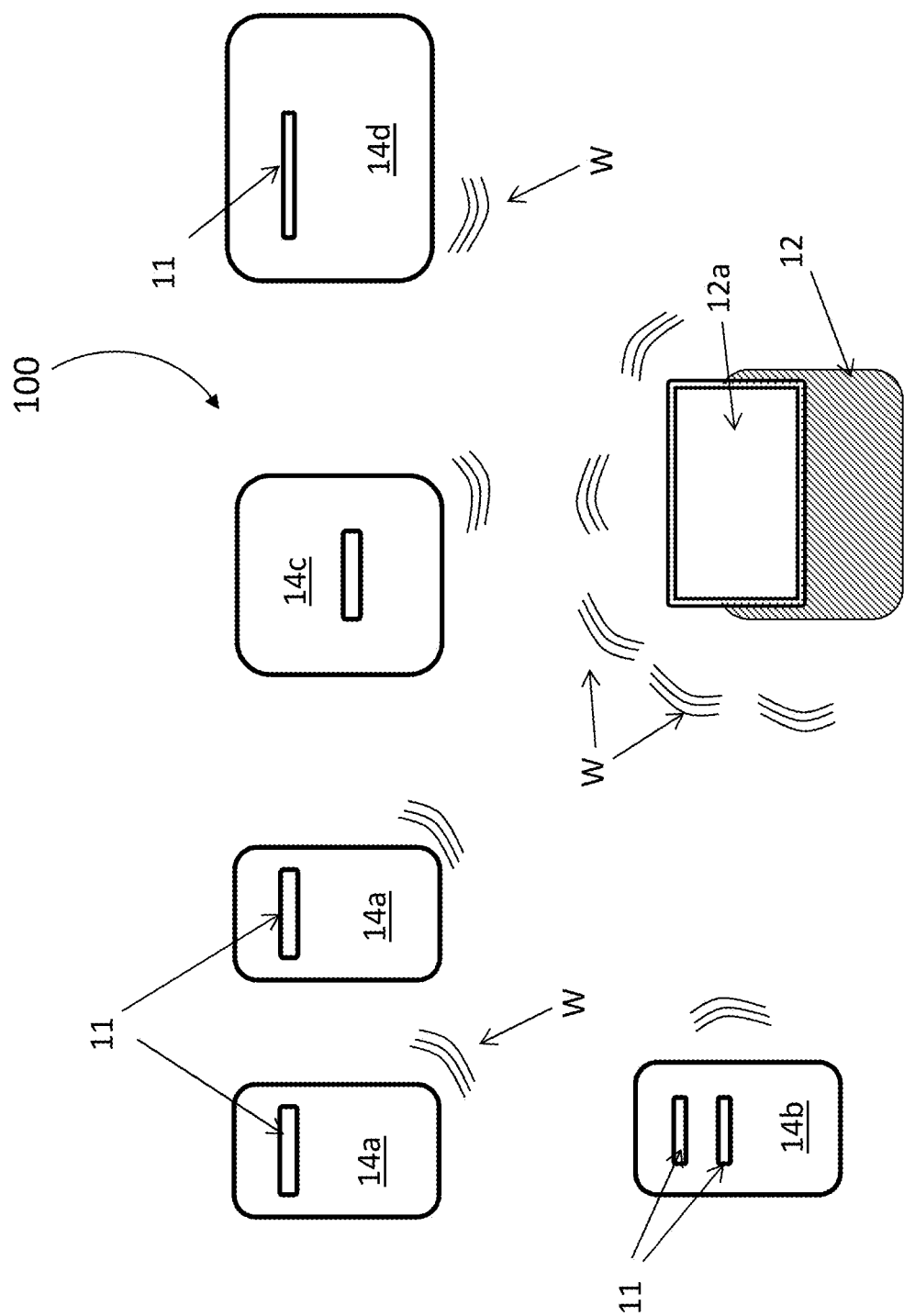
Figure 3:
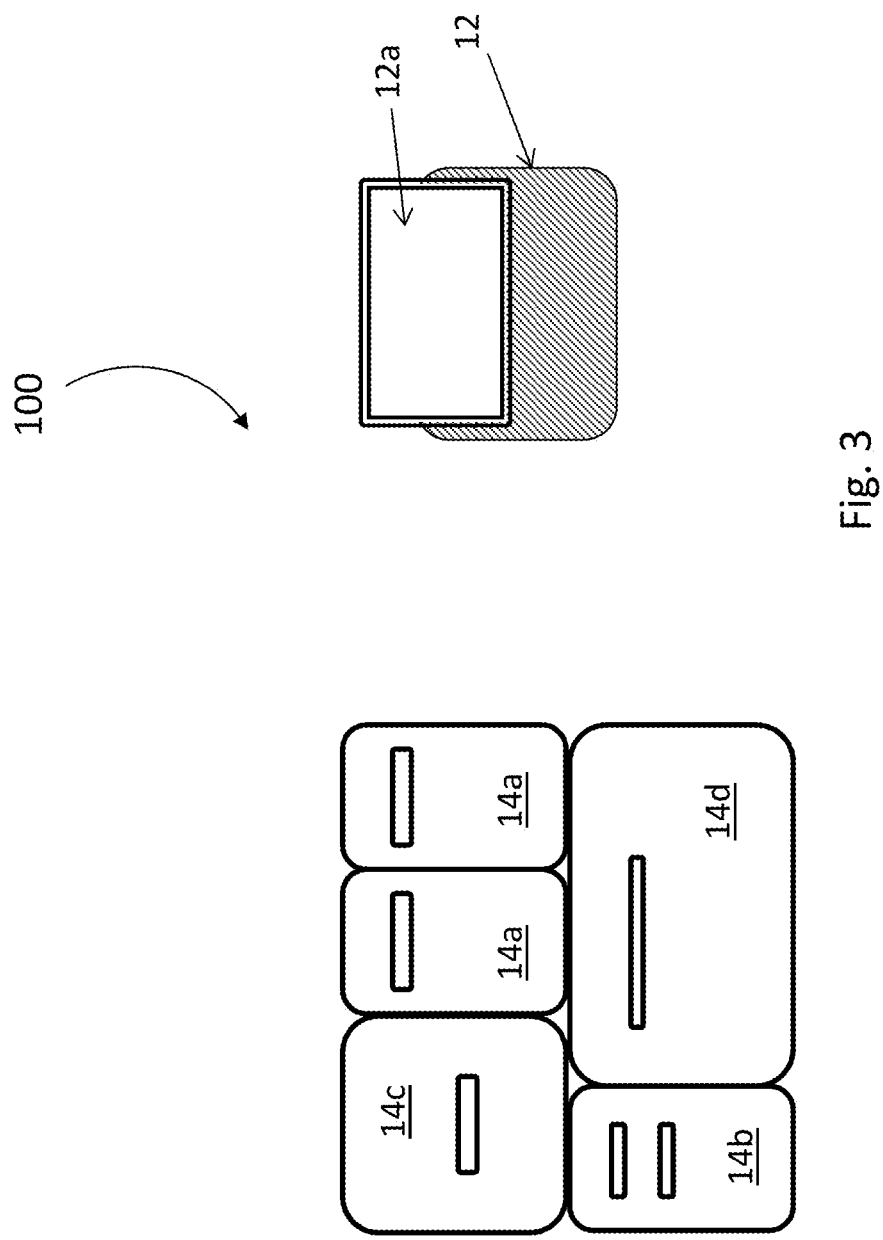
Figure 5:
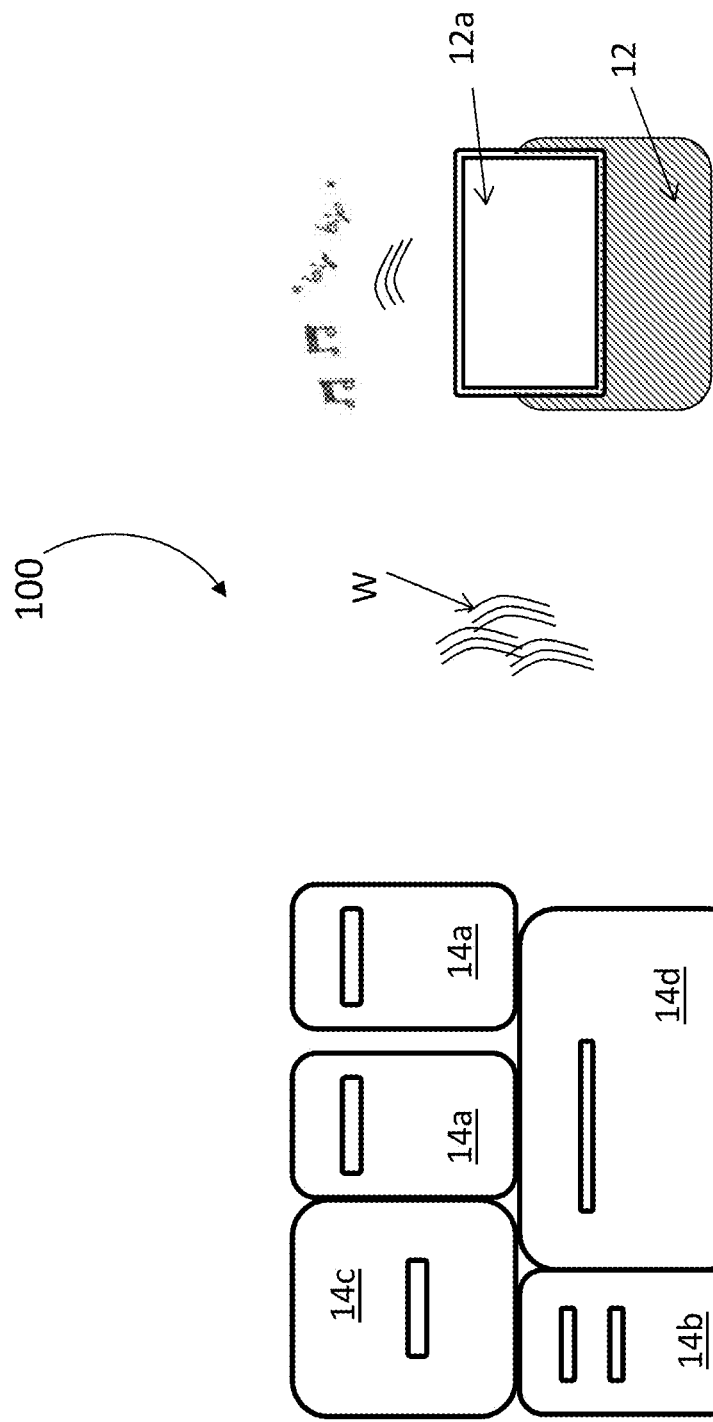
Figure 6:
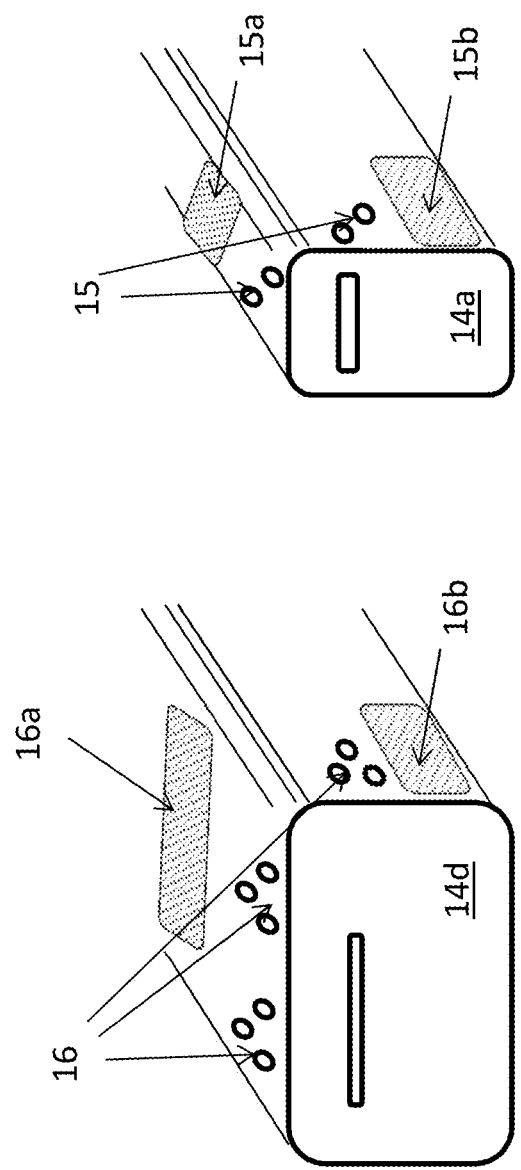
Figure 8:
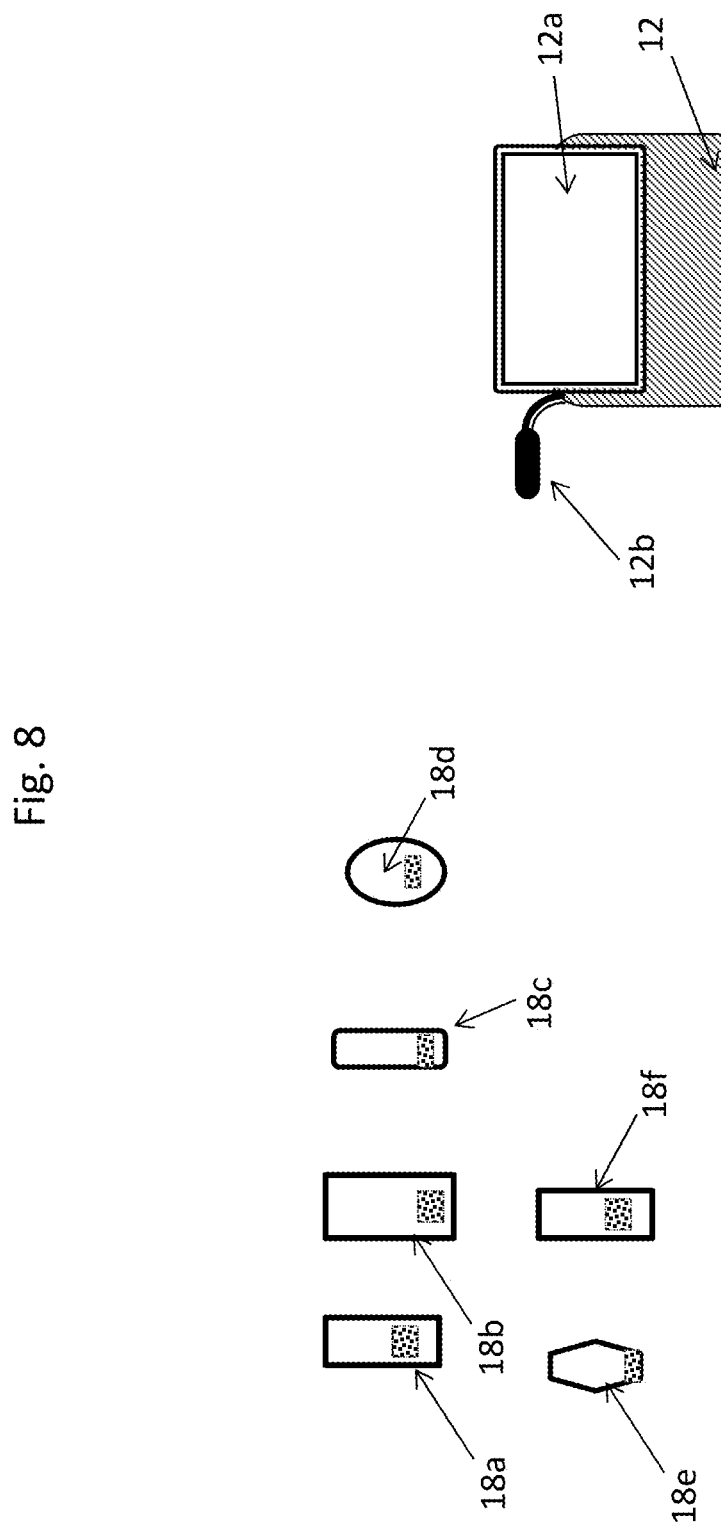
Figure 9:
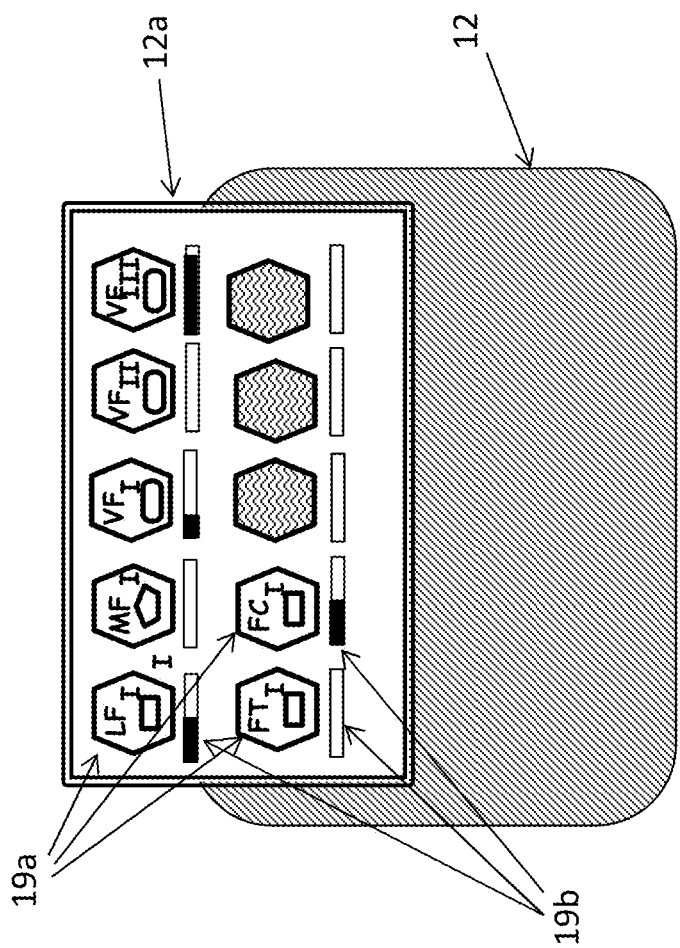

Having thus described various embodiments of the present disclosure in general terms, reference will now be made to the accompanying drawings, which are not necessarily drawn to scale, and wherein:

FIG. 1 is a perspective view of a reader module, according to one aspect of the present disclosure;

FIG. 2 is a schematic illustration a diagnostic test reader system, according to one aspect of the present disclosure;

FIG. 3 is a schematic illustration of a diagnostic test reader system according to present disclosure where the reader modules are stacked;

FIG. 4 is a schematic illustration of a diagnostic test reader system according to present disclosure where the reader modules are incorrectly stacked;

FIG. 5 is a schematic illustration of a diagnostic test reader system according to present disclosure where the reader modules are stacked, but where one of the reader modules has been pushed to an unstable position;

FIG. 6 illustrates sections of two reader modules with tactile sensors and fiducial marks;

FIG. 7 is a schematic illustration of a diagnostic test reader system according to present disclosure where the reader modules each comprise a radiofrequency sensor incorporating a transceiver, an electrical fiducial mark and a unique code and the mother comprises a radio frequency transceiver;

FIG. 8 illustrates a number of different diagnostic test cartridges each marked with a bar code as well as a mother module comprising a bar code reader;

FIG. 9 shows a mother module with a screen with a graphical user interface comprising icons for the reader modules with an indicator showing the operation status of each individual reader module;

FIG. 10 illustrates a reader module database;

FIG. 11 illustrates a user database;

FIG. 12 illustrates a diagnostic test cartridges database; and

FIG. 13 illustrates a patient database.

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

The present disclosure provides a diagnostic test reader system which is flexible and relatively simple to use and which can be used for reading two or more rapid diagnostic test cartridge types. According to various aspects, the present disclosure may provide a diagnostic test reader system which alleviates at least one of the problems discussed above.

The diagnostic test reader system may be adapted for use by respective clinics. These and other problems have been solved by the present disclosure as disclosed hereinbelow.

The diagnostic test reader system of the present disclosure provides flexibility and simple handling of rapid diagnostic test types, thereby providing a large improvement to both smaller as well as large clinics. The diagnostic test reader system provides a more effective use of the readers.

The diagnostic test reader system may include a plurality of modules, where the modules may include a plurality of reader modules and at least one mother module. The term plurality is herein used to mean at least two unless otherwise specified or clear from the context.

Each of the reader modules may have a unique code and is adapted for reading a specific test cartridge type. Each of the reader modules may be adapted to be in data communication with the mother module for receiving instructions from the mother module and for transmitting read and/or derived data to the mother module. The mother module may be configured for communicating individually with each of the reader modules.

Thus, by use of the one single mother module of the diagnostic test reader system all of the individual reader modules of the diagnostic test reader system may be controlled or operated.

The operator such as a doctor, a veterinarian or an assistant may thus be informed by the mother module which reader modules are free and preferably also be informed about the state of operation of the respective reader modules so as to know when a reader module is expected to be free. In some instances, the operator may reserve a reader module for a selected time slot. The mother module may then mark the reader module as reserved for the time slot in question. The term "user" includes an operator.

The mother module may be advantageously configured for recognizing each of the reader modules of the diagnostic test reader system via the unique code of the specific reader module. Advantageously the mother module may also comprise a unique code. Thus the operator may purchase the mother module and the reader modules separately and combine them, such that the mother module is associated with each reader module and each reader module is associated with the mother module. The mother module and the reader module may each have a computer programmed to perform the association and storing the association between mother and reader modules. Advantageously the mother module and each reader module may be configured for wireless communication, such as, for example, using Bluetooth technology.

The modules may be programmed to find other modules within a preselected distance such as, for example, within 1, 2, 10 meters or longer, and upon instruction from an operator to lock and store selected modules together to form a diagnostic test reader system having at least one mother module mutually associated with each of a plurality of reader modules.

Thus, in one aspect of the diagnostic test reader system of the present disclosure the system may have at least one mother module mutually associated with each of a plurality of reader modules wherein the mutual association entails that each reader module stores the unique code of the mother module and is configured for recognising and communicating with the mother module and the mother module stores the unique code of each of the reader modules and is configured for communicating individually with each of the reader modules.

The term "substantially" should herein be taken to mean that ordinary product variances and tolerances are included.

The term "about" is generally used to include what is within measurement uncertainties. When used in ranges the term "about" should herein be taken to mean that what is within measurement uncertainties is included in the range.

The term "liquid sample" or "sample" or "test liquid" means any liquid containing sample including liquid sample comprising solid parts, such as dispersions and suspensions. The sample comprises liquid at the time of performing the method.

Throughout the description or claims, the singular encompasses the plural unless otherwise specified or required by the context.

The terms "test" and "assay" are used interchangeably.

The terms "configured for" or "configured to" are herein used to mean that the item in question is specifically constructed, designed or programmed to perform the purpose in question.

In another aspect, the mother module may be configured for transmitting instructions to each individual reader module such as, for example, instructions for start running a test procedure, for performing a test procedure in a preselected way or with preselected timing. In another aspect, the mother module may be configured for receiving software updates for one or more of the reader modules and for transmitting the software updates to each selected reader module, which reader module(s) may be selected by an operator or by having software to be updated by the received software update (i.e. of same software type but of an earlier version). The mother module may advantageously be programmed to transmit received software updates within a preselected software update time slot.

Advantageously the reader modules may be physically separate boxes comprising separate electronic circuits and drivers for performing respective diagnostic tests. Each reader module may have a slot for receiving respective test cartridges. Usually a reader module may have one single slot for receiving a test cartridge. However, in some instances, one or more of the reader modules may each comprise two or more slots for receiving diagnostic test cartridges, preferably diagnostic test cartridges of the same type. Such reader modules having two or more slots for receiving diagnostic test cartridges may advantageously be configured for performing double tests and or for multiplexing tests.

Each reader module may be individually movable and advantageously have a size (height, width, and depth) up to about 0.5×1×0.5 m. Typically, the reader modules may each have a size of from about 0.001 to about 0.25 m$^3$, such as from about 0.08 to about 0.2 m$^3$. The reader module may have the same or different size. In some instances, the reader module may comprise two or more reader modules of different size.

Advantageously at least one of the reader modules may include a sensor for detecting position data representing its spatial position relative to at least one other of the reader modules. The sensor of the at least one reader module may preferably be configured for transmitting the position data comprising the respective spatial position relative to the at least one other of the reader modules to the mother module.

At least one other of the reader modules may include one or more fiducial marks detectable by said sensor. In some instances, each reader module may have one or more fiducial marks detectable by said sensor. The one or more fiducial marks may, for example, form part of or be incorporated into the respective sensors of the reader modules. Advantageously the sensor of the respective reader module(s) may be configured for detecting the position data representing its spatial position relative to at least one other of the reader modules by detecting the one or more fiducial marks of said at least one other reader module.

The sensor on the reader module may be advantageously located on a predefined position on the reader module and, thus, when the sensor detects the position data representing the spatial position of the sensor relative to at least one other of the reader modules, the relative position between the reader modules may be determined based on the position data. In some instances, the mother module may be configured for receiving the position data and for determining the relative position between two or more reader modules based on the position data.

Advantageously, the sensor on the reader module may be configured for sensing the unique code of the at least one other module.

In one aspect, the sensor of at least one and preferably of each reader module may be configured for transmitting the detected unique code of at least one other of the reader modules to the mother module.

The unique code of each of the respective reader modules may be stored in a chip which may advantageously be located at a known position of the respective reader modules. One or more, or all of the reader modules advantageously may have a sensor-chip set located at a preselected position on the respective reader modules, wherein the mother module has a database or is in data communication with a database storing information about the location of the sensor-chip set of the respective reader modules. The location of the sensor-chip set of the respective reader modules may advantageously be associated with the unique code stored in the respective chip.

In one aspect, the sensor of the at least one reader module may be configured for detecting position data representing its spatial position relative to at least one other of the reader modules when the reader modules are within a predefined distance to each other, such as within a distance of up to about 10 cm.

In another aspect, the sensor of the at least one reader module may be configured for detecting position data representing its spatial position relative to at least one other of the reader modules when the reader modules are in physical contact with each other, e.g. by being arranged in a side by side configuration or in a stacked configuration. In another aspect, the sensor of each reader module may be configured for detecting position data representing its spatial position relative to one or more other of the reader when the reader modules are within a predefined distance to each other, such as within a distance of up to about 10 cm or even in physical contact with each other.

Advantageously the sensor of a reader module or the sensor of each reader module may be configured for transmitting the determined position data to the mother module and the mother module is configured for determining the relative position between two or more, or all of the reader modules of the diagnostic test reader system.

The mother module may then at any time know the relative position of the reader modules and the mother module may thus advantageously inform an operator, for example, via a user interface, about which reader module to use for performing a given diagnostic test and where this particular reader module is positioned relative to the other reader modules. Thus, the risk of inserting a diagnostic test cartridge into an incorrect reader module is highly reduced and the administration and control of the use of the various reader modules are highly improved.

Advantageously the mother module may be configured to warn an operator if a reader module is out of order, is during service and/or is during software update and simultaneously inform the operator about the position of the reader module in question and optionally inform the operator when the reader module is expected to be ready for operation again.

Further, if a new reader module has been added to the diagnostic test reader system and has been mutually associated with the mother module, the mother module may inform the operator about the position of this newly added reader module.

Advantageously the sensor or each sensor of the one or more reader modules may be configured for detecting orientation data representing the relative orientation between the respective modules and for transmitting the orientation data to the mother module. The mother module may be advantageously configured for determining the relative orientation between two or more reader modules based on the orientation data.

The phrase that the sensor is configured for "detecting position data" is herein used to mean that the sensor is configured for detecting a part of another reader module, usually a sensor on the other module or another detectable fiducial mark positioned on or incorporated into the reader module and based on this for generating the position data representing the relative orientation between the sensor in question and the reader module carrying the sensed fiducial mark, for example, the sensor of the other reader module.

The fiducial marks of the respective reader modules may be advantageously configured to have an orientation which is detectable by the sensor such that the sensor can detect the orientation of the fiducial mark and thus detect the orientation data representing the relative orientation between the respective modules.

Each reader module may carry one or more detectable fiducial marks, which may be optically detectable fiducial marks, electrically detectable fiducial marks, magnetically detectable fiducial marks depending on the sensor adapted to detect the fiducial mark(s). Advantageously the fiducial mark(s) may form part of or may be integrated with the sensor of the reader module.

The term "fiducial mark" is herein used to mean a fiducial mark which is detectable by the sensor, for example optically, electrically, magnetically and/or electronically detectable by the sensor. The fiducial mark(s) may be on the outer surface of the respective reader module(s) and/or it may be incorporated or integrated with the respective reader module(s)

The phrase that the sensor is configured for "detecting orientation data" is herein used to mean that the sensor is configured for detecting a part of another reader module, usually a sensor on the other module or another detectable fiducial mark positioned on or incorporated into the reader module and based on this for generating the orientation data representing the relative orientation between the sensor in question and the reader module carrying the sensed node, for example the sensor of the other reader module.

In one aspect, the sensor of at least one and preferably each of the reader modules is configured for detecting position data representing its spatial position relative to at least one other of the reader modules, sensing the unique code of the same of the at least one other of the reader modules, and transmitting at least one set of neighbour data, wherein each set of neighbour data comprises the position data and the unique code of the same reader module. In one aspect, the sensor of the reader module may be configured for transmitting at least one set of neighbour data, each set of neighbour data having the unique code of the other reader module and position data.

The sensor may include a transmitter for wireless transmission of position data and optional orientation data.

In some instances, each set of neighbour data may include position data representing the spatial position of the sensor relative to one other reader module associated with the unique code of the same other reader module.

In other instances, each set of neighbour data may include position data representing the spatial position of the sensor relative to one other reader module associated with the unique code of the same other reader module. In one aspect, each set of neighbour data may include position data representing the spatial position of the sensor relative to one other reader module associated with the unique code of the same other reader module and orientation data representing the relative orientation between the module having the sensor and the reader module associated with the unique code.

In one aspect, at least two of the reader modules each may include a sensor for detecting position data representing its spatial position relative to at least one other of the reader modules and preferably for detecting orientation data representing the relative orientation of the sensor to at least one other of the reader modules. The respective sensors of the respective reader modules may be configured for transmitting the detected position data and optionally the detected orientation data to the mother module.

In one aspect, each sensor may be advantageously configured for detecting position data representing its spatial position relative to at least one other of the reader modules together with the unique code of the at least one other of the reader modules and for generating and transmitting the data as one or more sets of neighbour data, wherein each set includes the position data representing the spatial position of the sensor relative to one other reader module associated with the unique code of the same other reader module. Advantageously each set of neighbour data may also include orientation data as described above.

The sensor(s) of the reader module(s) may in principle be any kind of short range sensor, such as a tactile sensor, an optical sensor, a magnetic sensor or a radio-frequency sensor, such as a chip sensor (RFID-active or passive) or a Bluetooth sensor.

The unique code may advantageously be incorporated or associated with the sensor. In one aspect, the sensor may be configured for sensing sensors and position and/or orientation of sensors located on other of the reader modules of the diagnostic test reader system. In another aspect, the reader module(s) each may include two or more sensors. This is in particular advantageous where the sensors are adapted for detecting orientation data representing relative orientation of the reader modules. Optical sensors are also suitable for detecting orientation data.

In one aspect, the sensor may include a tactile sensor such as a touch sensor (e.g. a button or a mechanical microswitch), where an applied force such as from a neighbouring reader module in physical contact with the reader module carrying the tactile sensor may apply a detectable force. The tactile sensor may be a binary sensor or an array of binary sensors, wherein the activated binary sensors may identify the unique code of the reader module which has activated the binary sensors. The reader module positioned in contact with (e.g. stacked onto the reader module carrying the textile sensor) other reader module may include a detectable fiducial mark in the form of a pattern of protrusions and/or depressions configured for activating one or more of the binary sensors. The detectable fiducial mark in the form of a pattern of protrusions and/or depressions may comprise the unique code which thereby is detectable by the tactile sensor upon contact with the fiducial mark.

In one aspect, the sensor may be an optical sensor having one or more photodiodes and wherein the other reader module or all of the reader modules carry detectable color codes or barcode fiducial marks detectable by the optical sensor. The color codes and/or the bar code(s) may also include the unique code of the respective reader module.

In one aspect, the sensor may be a magnetic sensor, such as a micromechanical (MEMS) sensor and the other reader module(s) may carry fiducial marks generating detectable magnetic field(s).

In one aspect, the sensor may be a radio-frequency sensor, such as a chip sensor (RFID-active or passive) or a Bluetooth sensor. The radio-frequency sensor may also constitute or provide a detectable fiducial mark and may also include the unique code of the respective reader module.

One of skill in the art will recognize that other types of sensors or combinations of sensors may be used. Where it is required for detecting the respective reader modules the reader modules advantageously may carry one or more detectable fiducial marks as described above.

In one aspect, the sensor may be or includes a transceiver. The transceiver may include said respective unique code. Optionally one or more of the reader modules may have one or more passive chips including the respective unique code.

The diagnostic test reader system may have as many reader modules as desired for the individual clinic. In some instances, the basic package of the diagnostic test reader system may include one mother module and two or more reader modules. The clinic can thereafter add as many reader modules to the diagnostic test reader system as desired and the types of reader modules may be individually selected according to the need of the individual clinic.

The diagnostic test reader system may include at least one mother module. However, if desired, the diagnostic test reader system may comprise two or more mother modules which may be in data communication with each other and may be synchronized.

In one aspect, the system may include at least 3 reader modules, at least 4 reader modules, at least 5 reader modules, or from 4 to 20 reader modules.

The reader modules may include any type of reader module suitable for reading an associated type of diagnostic test cartridges suitable for performing a rapid diagnostic test type. A diagnostic test cartridge type is defined to include any type of diagnostic test cartridges for performing a diagnostic test within two hours or less, e.g. a single step diagnostic test cartridge and/or a point-of-care diagnostic test cartridge. Many of the rapid diagnostic test cartridge types are suitable for performing a diagnostic test very fast, such as within 30 minutes or less, within 10 minutes or less, within 5 minutes or less or even within one minute or less. Reader module(s) for such types of rapid diagnostic test cartridge types are in particularly preferred for use in accordance with the present disclosure.

Examples of reader modules include but are not limited to a microfluidic test cartridge reader module, a lateral flow test cartridge reader module, a vertical flow test cartridge reader, a fluorescent test cartridge reader module, a flow through test cartridge reader module, a flow cytometry cartridge reader module, an electrical read out test cartridge reader module, an imaging read out cartridge reader module, an electrochemical read out cartridge reader module, a light absorption cartridge reader module, magnetically assisted cartridge reader module, a snap type cartridge test or a combination thereof.

One or more of the reader modules may advantageously comprise an illumination arrangement and an optical reader, such as a photodiode or a camera e.g. a CMOS or a CDD camera and/or a video camera.

The reader module may comprise two or more of the abovementioned reader module types.

The vertical flow test cartridge reader type may for example be a reader for a vertical flow test cartridge as described in "Vertical flow immunoassay (VFA) biosensor for a rapid one-step immunoassay" by Oh Y. K et al. Lab Chip. 2013 Mar. 7; 13(5):768-72. doi: 10.1039/c21c41016h. Epub 2013 Jan. 9. In some instances, the vertical flow test cartridge reader type may for example be a reader for a Rapid Vertical Flow cartridge marketed by MedMira or as described in US2011256638.

The vertical flow test cartridge reader type may for example be a reader for a snap test assay cartridge as described by "Thomas P. O'Connor in "SNAP assay technology" Topics in Compan An Med 30(2015) 132-138 and/or reader for a snap test assay cartridge as marketed by IDEXX Europe B.V. The Netherlands.

In one aspect, the diagnostic test reader system may include two or more of the same reader module types. Due to the flexibility of the system a clinic may add as many same type reader modules to the diagnostic test reader system as desired. For many veterinarian clinics it may be desired that the diagnostic test reader system has two or more lateral flow test cartridge reader modules because there have been developed and marketed diagnostic lateral flow test cartridges for many different target analytes, such as analytes selected from protein(s), peptide(s), antigen(s) and other biological molecule(s).

In one aspect, the diagnostic test reader system has two or more different reader module types, at least three different reader module types, or at least four different reader module types.

The diagnostic test reader system may for example include a mother module, a microfluidic test cartridge reader module, a lateral flow test cartridge reader module and a vertical flow test cartridge reader.

In one aspect, each reader module of the same type may have an identical visual tag coding for the reader module type. In some instances, each reader module of the same type may have an identical color coding for the reader module type.

The visual tag may form or form part of a fiducial mark detectable by the sensor as described above. The unique code of the respective reader module may be incorporated in the tag or be included in another visual tag and/or a chip.

Advantageously the reader modules may be adapted to be stacked, for example in two rows, three rows or more rows. Due to the sensors and the fiducial marks on the respective reader module, the mother module may be configured for determining the relative spatial position of the respective reader modules and thus how the reader modules are stacked and the relative position and preferably orientation of each reader module in the stack of reader modules.

As mentioned above, the respective reader module may have equal or different size and optionally also differ in weight and sensitivity and thus it may be important that the reader modules are stacked or positioned in a preselected order and the mother module is advantageously configured to control if the positioning of the various reader modules is acceptable and provide for an acceptable operation of the respective reader modules.

Advantageously, the reader modules of a diagnostic test reader system may have the same heights and/or same depth, whereas the width may differ. Thus, in some instance the reader modules may have the same height. Advantageously, the widths of the respective reader modules may be either the smallest width referred to as base-width or X times the base-width, wherein X is 0.5 or an integer or an integer+0.5. Thereby, a very stable stack of reader modules may be provided even where the sizes of the reader modules differ.

In one aspect, the mother module may be configured for determining the relative spatial positions and optionally orientation of the reader modules and the mother module is further configured to determine if the relative spatial positions and optional orientations of the reader modules fulfil at least one predefined requirement. The at least one predefined requirement may be fulfilled when the reader modules are stacked in a predefined configuration. The at least one predefined requirement may include at least one pre-programmed requirement and/or at least one user selectable requirement.

It may be desired that the predefined requirement(s) be selected by the operators at the clinic, not only to ensure the high flexibility of the diagnostic test reader system to adapt the diagnostic test reader system to the needs of the operator (s) at the clinic, but also to ensure a safe and stable stacking. It has been found that some reader modules may be more sensitive than others, for example due to vibrations, some reader modules being heavier than others, some reader modules requiring that the diagnostic test cartridge is pressed into its slot with higher force than others. Such differences may be accounted for when selecting the pre-defined requirement(s). The predefined requirement(s) may be submitted to the mother module by arranging the reader modules in the desired stacked configuration, setting the mother module to a programming of stacking mode, instructing the mother module that the present stacked configuration is the desired stacked configuration and the mother module may store stacking data representing the desired stacked configuration and using these stacking data as the predefined requirement(s).

In one aspect, the mother module may be configured for determining the relative spatial positions of the reader modules at least partly via the sensors of the respective reader modules.

In one aspect, the mother module may be configured for receiving one or more sets of neighbour data and based on the received sets of neighbour data determining the relative spatial positions of the reader modules and determining if the relative spatial positions of the reader modules fulfil the predefined requirement.

In one aspect, the mother module may be configured for triggering an alarm if the at least one predefined requirement is not fulfilled, the alarm being a visual alarm and/or an audible alarm.

Thus, if a reader module is positioned in an incorrect position in the stack of reader modules, if two reader modules are switched in position, if a reader module is missing and/or if a reader module becomes misaligned or is about to fall out from the stack, the alarm may be triggered. If a reader module is to be removed from the stack of reader modules, the predefined requirement stored by the mother module may be temporarily modified.

Advantageously, the mother module may be in data communication with one or more databases for requesting data and/or for storing data. The one or more data bases may be web based data bases or locally stored data bases.

In one aspect, the mother module may be associated with a user interface. The user interface may be any kind of user interface, such as an interface comprising at least one of a screen, a keyboard, an audible user interface, a video interface and/or a printer, such as a touch screen and/or a graphical user interface preferably in combination with a printer. The user interface may include at least one screen.

In one aspect, the mother module may be associated with a screen with a graphical user interface having an icon for each of the reader modules including an indication showing if the respective reader module is operating and may include a time indicator indicating when the respective operating reader is expected to terminate its present operation.

The phrase that "a reader module is operating" or is "in operation" means that a test is running, is about to be initiated and/or that a diagnostic test cartridge is inserted into the slot of the reader module.

In one aspect, the mother module may be in data communication with a user database. The user database may include user identification and associated user authorization for each user, the user authorization preferably comprises an indication of at least one reader module which a user with the associated user identification is qualified for using.

In one aspect, at least one of the test modules may determine that a user has a user authorization registered in the user database and that the user is approved by the mother module such as, for example, by presenting a user code such as in the form of a pin code, a chip and/or a bar code.

The mother module may include a bar code reader or may be in data communication with a bar code reader. The bar code reader may for example be applied for reading a user bar code, a patient bar code and/or a diagnostic test cartridge bar code. After having read a bar code the mother module may be configured for requesting data associated with the read bar code from a data base.

In one aspect, the mother module may be in data communication with a cartridge database. The cartridge database may include cartridge identification and associated reader module data providing that when identifying a cartridge to the mother module, the mother module is configured for assigning a reader module for operating a given test using the cartridge. Preferably the identification of the cartridge may include reading the barcode associated with the cartridge by the bar code reader.

In one aspect, the mother module may be in data communication with a patient database. The patient database may include patient identification associated with patient data for a plurality of patients. The mother module may be configured for storing a test result of a specific patient in the patient database and providing that the test result is associated with the specific patient. The test result may be transmitted to the mother module by a reader module that has run the test.

In one aspect, the mother module may be configured for extracting data from the patient database and transmitting the data to a reader module for running a test.

In one aspect, the mother module may be configured for extracting data from a general statistics patient database and transmitting the data to a reader module for running a test.

In one aspect, the mother module may be in connection with the internet, in contact with one or more web databases, where at least a general statistics patient database is a web database.

In one aspect, at least one of the reader modules may be configured for transmitting a test initiating signal upon sensing that a cartridge has been inserted into its slot. The reader module may be configured for transmitting test status to the mother module including progress of a test running on the cartridge.

All features of the present disclosure, including ranges and preferred ranges, can be combined in various ways within the scope of the disclosure, unless there are specific reasons not to combine such features.

The reader module of FIG. 1 illustrates an example of a reader module 14 of a diagnostic test reader system according to aspects of the present disclosure. The reader module has a flat top, bottom and sides. As shown in the following examples this flat face may ensure easy stacking and may further provide support for tactile sensors and fiducial marks. As shown, the reader module may have a width W, a height H and a depth D. The reader module may have a slot 1 for insertion of a diagnostic test cartridge for running a test procedure.

FIG. 2 shows a number of reader modules, 14a, 14b, 14c, 14d and a mother module 12 of a diagnostic test reader system 100. In this instance, the diagnostic test reader system may have two reader modules 14a of a first type and one of each of three other types of reader modules 14b, 14c, 14d.

Each of the reader modules, 14a, 14b, 14c, 14d may include at least one slot 11 and one of the reader modules 14b may have two slots for carrying parallel tests as described above.

The reader modules, 14a, 14b, 14c, 14d are seen in front view and it can be seen that the reader modules, 14a, 14b, 14c, 14d may have equal height, whereas they may differ in width. Some of the reader modules 14a, 14b may have the smallest width, referred to as base-width. One of the reader modules 14c may have a width corresponding to 1.5 times the base-width and one of the reader modules 14d may have a width corresponding to 2 times the base-width. Thereby, the reader modules, 14a, 14b, 14c, 14d may be stacked in a very stable arrangement.

The depth of the reader modules, 14a, 14b, 14c, 14d may or may not differ. Advantageously the depth of the reader modules, 14a, 14b, 14c, 14d may be within a variation of 50% of the smallest depth, or preferably within a variation of 25% of the smallest depth.

Each of the reader modules may include a unique code and may be adapted for reading a specific test cartridge type.

The mother module 12 may include a screen 12a providing a user interface.

As indicated with the waves W, the mother module may be configured for communicating individually with each of the reader module as described further above.

FIG. 3 shows the reader modules, 14a, 14b, 14c, 14d stacked in a desired arrangement. As it can be seen, the stack of reader modules, 14a, 14b, 14c, 14d may be very stable. In some instances, the mother module 12 is not in the stack but may be positioned at a distance from the stack of reader modules, 14a, 14b, 14c, 14d such as for example at a desk.

FIG. 4 shows the reader modules, 14a, 14b, 14c, 14d stacked in an undesired or incorrect arrangement.

The mother module 12 may be configured for determining the relative spatial positions of the reader modules, and for determining if the relative spatial positions of the reader modules fulfil at least one predefined requirement, which for example may include that the reader modules, 14a, 14b, 14c, 14d should be stacked as in FIG. 3. As the mother module 12 detects that the stacking is incorrect it may send out an audible alarm. The mother module 12 may instead of or in addition to the audible alarm, send out a visual alarm on its screen 12a.

FIG. 5 shows the reader modules, 14a, 14b, 14c, 14d stacked in a desired arrangement but where one of the reader modules 14a has been pushed to an unstable position.

Since the mother module 12 may be configured for determining the relative spatial positions of the reader modules, and for determining if the relative spatial positions of the reader modules fulfil at least one predefined requirement including that the reader modules, 14a, 14b, 14c, 14d should be stacked as in FIG. 3, the mother module 12 may immediately detect that the reader module 14a has been pushed to an unstable position and send out an audible alarm as shown.

FIG. 6 shows a part of two of the reader modules 14d, 14a in perspective. It can be seen that the reader modules 14d, 14a at their top face and side have fiducial marks 15, 16 coding for the respective reader modules 14d, 14a and tactile sensors 15a, 16a for sensing fiducial marks of neighbor reader modules. The reader modules 14d, 14a also have tactile sensors and fiducial markers on their not shown side and on their bottom face. Left side tactile sensors are positioned to sense right side fiducial marks, right side tactile sensors are positioned to sense right side fiducial marks, bottom tactile sensors are positioned to sense top fiducial marks and top tactile sensors are positioned to sense bottom fiducial marks.

FIG. 7 illustrates an aspect where the reader modules, 14a, 14b, 14c, 14d each include a radiofrequency sensor 17a incorporating a transceiver, an electrical fiducial mark and a unique code and where the mother module includes a radio frequency transceiver.

The fiducial marks may be configured to have an orientation which is detectable by the sensors of the other reader modules such that the sensors may detect the orientation of the fiducial mark and thus detect the orientation data representing the relative orientation between the respective modules.

The mother module 12 may have a transceiver 17b for individually communicating with the respective reader modules, 14a, 14b, 14c, 14d.

In one aspect, the sensor may include a radio-frequency sensor, such as a chip sensor (RFID-active or passive) or a Bluetooth sensor. The radio-frequency sensor may also constitute or provide a detectable fiducial mark and may also include the unique code of the respective reader module.

The mother module 12 may advantageously comprise a bar code reader 12 as illustrated in FIG. 8. The bar code reader 12b may advantageously be adapted to read the bar code of respective diagnostic test cartridges such as the various diagnostic test cartridges 18a, 18b, 18c, 18d, 18e, 18f carrying a bar code as shown.

The mother module 12 shown in FIG. 9 has a screen 12a with a graphical user interface having an icon 19a for each of the reader modules. Beneath the respective icons 19a the screen displays an indicator 19b showing the operation status of each individual reader module. Thereby, the user may immediately observe if a reader module is operating, the status of the reader module and when it is expected to finish a procedure in progress.

FIGS. 10-13 illustrate examples of databases which the mother module may be in data communication with as described above.

Many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

The invention claimed is:

1. A diagnostic test reader system comprising a plurality of modules, including a plurality of reader modules and at least one mother module, each of the reader modules having a unique code and being programmed to read a specific test cartridge type, each of the reader modules being in data communication with the mother module for receiving instructions from the mother module and for transmitting at least one of read and derived data to the mother module, the mother module being programmed to communicate individually with each of the reader modules, wherein the reader modules are physically separate boxes each having separate electronic circuits and drivers for performing respective diagnostic tests, each reader module having a slot for receiving respective test cartridges, and further wherein at least one of the reader modules comprises a sensor programmed to detect position data and determine its spatial position relative to at least one other of the reader modules, said sensor of said at least one reader module being programmed to transmit said position data comprising said respective spatial position relative to at least one other of the reader modules to said mother module, wherein at least one other of the reader modules has one or more fiducial marks detectable by said sensor, and further wherein the mother module is programmed to determine the relative spatial positions of the reader modules.

2. The reader system of claim 1, wherein said sensor of said reader module is configured for detecting position data representing its spatial position relative to at least one other of the reader modules when it is arranged within a distance of up to about 10 CM.

3. The reader system of claim 2, wherein said sensor of the reader module is configured to detect a unique code of at least one other of the reader modules, wherein said sensor is configured for transmitting said detected unique code of at least one other of the reader modules to the mother module.

4. The reader system of claim 3, wherein said sensor is configured for detecting position data representing its spatial position relative to at least one other of the reader modules, sensing said unique code of said same of the at least one other of the reader modules and transmitting at least one set of neighbour data, wherein each set of neighbour data comprises said position data and said unique code of said same reader module.

5. The reader system of claim 4, wherein the sensor or each sensor of the one or more reader modules is configured for detecting orientation data representing the relative orientation between the respective modules and for transmitting the orientation data to the mother module, wherein the mother module is configured for determining the relative orientation between two or more reader modules based on said orientation data.

6. The reader system of claim 5, wherein each set of neighbour data comprises position data representing the spatial position of the sensor relative to one other reader module associated with said unique code of said same other reader module, each set of neighbour data comprising position data representing the spatial position of the sensor relative to one other reader module associated with said unique code of said same other reader module and orientation data representing the relative orientation between the module comprising said sensor and the reader module associated with said unique code.

7. The reader system of claim 1, wherein at least two of the reader modules each comprise a sensor for detecting position data representing its spatial position relative to at least one other of the reader modules, said respective sensors of said respective reader modules being configured for transmitting said position data comprising position data representing said respective spatial position relative to at least one other of the reader modules to said mother module.

8. The reader system of claim 7, wherein each sensor is configured for detecting position data representing its spatial position relative to at least one other of the reader modules together with a unique code of said at least one other of the reader modules and for generating and transmitting at least one set of neighbour data, each set of neighbour data comprises said position data representing said spatial position of the sensor relative to one other reader module associated with said unique code of said same other reader module.

9. The reader system of claim 8, wherein said sensor comprises a transceiver comprising said respective unique code, wherein one or more of said reader modules comprise one or more passive chips comprising said respective unique code.

10. The reader system of claim 1, wherein said mother module is programmed to determine if the relative spatial positions of said reader modules fulfil at least one predefined requirement, wherein said at least one predefined requirement is fulfilled when the reader modules are stacked in a predefined configuration, said at least one predefined requirement comprises at least one pre-programmed requirement or at least one user selectable requirement.

11. The reader system of claim 10, wherein said mother module is configured for receiving one or more sets of neighbour data and based on said received sets of neighbour determining the relative spatial positions of said reader modules and determining if the relative spatial positions of said reader modules fulfil the predefined requirement.

12. The reader system of claim 10, wherein said mother module is configured for triggering an alarm if said at least one predefined requirement is not fulfilled, said alarm being at least one of a visual alarm and an audible alarm.

13. The reader system of claim 1, wherein said mother module is associated with a screen with a graphical user interface comprising an icon for each of the reader modules including an indication showing if the respective reader module is operating and further including a time indicator indicating when the respective operating reader is expected to terminate its present operation.

14. The reader system of claim 1, wherein said mother module is in data communication with a user database, said user database comprises user identification and associated user authorization for each user, the user authorization comprising an indication of at least one reader module which a user with the associated user identification is qualified for using.

15. The reader system of claim 14, wherein at least one of the test modules requires that a user has a user authorization registered in said user database and that said user is approved by said mother module by presenting a user code in the form of one of a pin code, a chip and a bar code.

16. The reader system of claim 15, wherein said mother module comprises a bar code reader.

17. The reader system of claim 1, wherein said mother module is in data communication with a cartridge database, said cartridge database comprises cartridge identification and associated reader module data, providing that when identifying a cartridge to said mother module, the mother module is configured for assigning a reader module for operating a given test using said cartridge, wherein said identification of said cartridge comprises reading a barcode associated with said cartridge by said bar code reader.

18. The reader system of claim 1, wherein said mother module is in data communication with a patient database, said patient database comprises patient identification associated with patient data for a plurality of patients, said mother module being configured to store a test result of a specific patient in said patient database and to ensure that the test result is associated with said specific patient.

19. The reader system of claim 1, wherein at least one of the reader modules is configured to transmit a test initiating signal upon sensing that a cartridge has been inserted into its slot, wherein said reader module is configured for transmitting test status to said mother module comprising progress of a test running on said cartridge.

* * * * *